United States Patent
Engler et al.

(10) Patent No.: US 11,965,120 B2
(45) Date of Patent: Apr. 23, 2024

(54) GEL ADHESIVE COMPRISING CROSSLINKED BLEND OF POLYDIORGANOSILOXANE AND ACRYLIC POLYMER

(71) Applicant: 3M INNOVATIVE PROPERTIES COMPANY, St. Paul, MN (US)

(72) Inventors: Amanda C. Engler, Woodbury, MN (US); Kiu-Yuen Tse, Woodbury, MN (US); Ramesh C. Kumar, Woodbury, MN (US); Adam R. Wohl, Mahtomedi, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 791 days.

(21) Appl. No.: 16/968,956

(22) PCT Filed: Apr. 3, 2019

(86) PCT No.: PCT/IB2019/052727
§ 371 (c)(1),
(2) Date: Aug. 11, 2020

(87) PCT Pub. No.: WO2019/193514
PCT Pub. Date: Oct. 10, 2019

(65) Prior Publication Data
US 2021/0009879 A1  Jan. 14, 2021

Related U.S. Application Data

(60) Provisional application No. 62/653,143, filed on Apr. 5, 2018.

(51) Int. Cl.
*C09J 183/10* (2006.01)
*A61L 15/22* (2006.01)
*A61L 15/58* (2006.01)

(52) U.S. Cl.
CPC ........... *C09J 183/10* (2013.01); *A61L 15/225* (2013.01); *A61L 15/585* (2013.01)

(58) Field of Classification Search
CPC ...... C09J 183/10; A61L 15/225; A61L 15/585
See application file for complete search history.

(56) References Cited

U.S. PATENT DOCUMENTS

| | | |
|---|---|---|
| 3,645,835 A | 2/1972 | Hodgson |
| 3,691,140 A | 9/1972 | Silver |
| 3,731,683 A | 5/1973 | Zaffaroni |
| 3,797,494 A | 3/1974 | Zaffaroni |
| 4,031,894 A | 6/1977 | Urquhart |
| 4,060,664 A | 11/1977 | McGuire |
| 4,166,152 A | 8/1979 | Baker |
| 4,336,243 A | 6/1982 | Sanvordeker |
| 4,595,001 A | 6/1986 | Potter |
| 4,619,979 A | 10/1986 | Kotnour |
| 4,636,432 A | 1/1987 | Shibano |
| 4,656,218 A | 4/1987 | Kinoshita |
| 4,838,253 A | 6/1989 | Brassington |
| 4,843,134 A | 6/1989 | Kotnour |
| 4,865,920 A | 9/1989 | Sweet |
| 5,045,569 A | 9/1991 | Delgado |
| 5,088,483 A | 2/1992 | Heinecke |
| 5,160,315 A | 11/1992 | Heinecke |
| 5,162,410 A | 11/1992 | Sweet |
| 5,474,783 A | 12/1995 | Miranda |
| 5,514,730 A | 5/1996 | Mazurek |
| 5,637,646 A | 6/1997 | Ellis |
| 5,656,286 A | 8/1997 | Miranda |
| 5,804,610 A | 9/1998 | Hamer |
| 5,866,222 A | 2/1999 | Seth |
| 5,891,076 A | 4/1999 | Fabo |
| 6,024,976 A | 2/2000 | Miranda |
| 6,051,747 A | 4/2000 | Lindqvist |
| 6,063,838 A | 5/2000 | Patnode |
| 6,221,383 B1 | 4/2001 | Miranda |
| 6,235,306 B1 | 5/2001 | Miranda |
| 6,465,004 B1 | 10/2002 | Rossi-Montero |
| 6,610,760 B2 | 8/2003 | Eckberg |
| 6,638,528 B1 | 10/2003 | Kanios |
| 7,407,709 B2 | 8/2008 | Zhou |
| 7,914,645 B2 | 3/2011 | Schalau |
| 7,968,661 B2 | 6/2011 | Ellis |
| 8,124,689 B2 | 2/2012 | Loubert |
| 8,221,863 B2 | 7/2012 | Keener |
| 8,295,960 B2 | 10/2012 | Cooper |

(Continued)

FOREIGN PATENT DOCUMENTS

| | | |
|---|---|---|
| EP | 0576544 | 1/1994 |
| EP | 0868498 | 10/1998 |

(Continued)

OTHER PUBLICATIONS

Billmeyer, Jr. "Textbook of Polymer Science", Wiley-Interscience, Second Edition, (1971), 84-85.

(Continued)

*Primary Examiner* — Michael P Cohen
(74) *Attorney, Agent, or Firm* — Jeffrey M. Olofson

(57) ABSTRACT

A method of making a silicone gel adhesive is described comprising providing an acrylic polymer, the acrylic polymer comprising at least 50 wt.-% of polymerized units of C1-C32 (meth)acrylate ester monomer; providing at least one non-functional polydiorganosiloxane, hydroxy-functional polydiorganosiloxane, or a mixture thereof; combining the acrylic polymer and polydiorganosiloxane into a mixture; coating the mixture onto a substrate, and subjecting the mixture to radiation thereby crosslinking the mixture. Also described is a silicone gel adhesive comprising a crosslinked material at least one non-functional polydiorganosiloxane, hydroxy-functional polydiorganosiloxane, or a mixture thereof; and an acrylic polymer comprising at least 50 wt.-% of polymerized units of alkyl (meth)acrylate monomers and a gel content of at least 20 wt.-%. Also described is a medical article or intermediate thereof, comprising a layer of the silicone gel adhesive described herein adhered to a substrate; and methods of adhering a medical article.

12 Claims, 1 Drawing Sheet

(56) References Cited

U.S. PATENT DOCUMENTS

| | | |
|---|---|---|
| 8,541,481 B2 | 9/2013 | Determan |
| 8,569,416 B2 | 10/2013 | Evans |
| 8,580,891 B2 | 11/2013 | Liu |
| 8,614,278 B2 | 12/2013 | Loubert |
| 8,822,559 B2 | 9/2014 | Zoller |
| 9,016,221 B2 | 4/2015 | Brennan |
| 9,017,771 B2 | 4/2015 | Determan |
| 9,121,307 B2 | 9/2015 | Aizenberg |
| 9,359,529 B2 | 6/2016 | Liu |
| 9,625,065 B2 | 4/2017 | Feldhahn |
| 9,890,302 B2 | 2/2018 | Tse |
| 10,398,406 B2 | 9/2019 | Keller |
| 2005/0282024 A1 | 12/2005 | Sherman |
| 2006/0115782 A1 | 6/2006 | Li |
| 2006/0173087 A1* | 8/2006 | Hyde .................. A61L 15/425 521/82 |
| 2006/0199151 A1 | 9/2006 | Hurson |
| 2007/0218276 A1 | 9/2007 | Hiramatsu |
| 2008/0044786 A1 | 2/2008 | Kalili |
| 2008/0295960 A1 | 12/2008 | Schalau, II |
| 2008/0319099 A1 | 12/2008 | Zhou |
| 2010/0267302 A1 | 10/2010 | Kantner |
| 2010/0331785 A1 | 12/2010 | Fabo |
| 2011/0206924 A1 | 8/2011 | Liu |
| 2011/0212325 A1 | 9/2011 | Determan |
| 2015/0299542 A1 | 10/2015 | Determan |
| 2015/0376345 A1 | 12/2015 | Liu |
| 2017/0100332 A1 | 4/2017 | Tonkin |
| 2018/0354161 A1 | 12/2018 | Gu |

FOREIGN PATENT DOCUMENTS

| | | | |
|---|---|---|---|
| EP | 1976956 | 10/2008 | |
| EP | 2421928 | 2/2012 | |
| EP | 2599847 | 6/2013 | |
| EP | 2636705 | 9/2013 | |
| EP | 2928978 | 10/2015 | |
| WO | WO 1996-002579 | 2/1996 | |
| WO | WO 1997-023577 | 7/1997 | |
| WO | WO 2000-068336 | 11/2000 | |
| WO | WO 2004-111151 | 12/2004 | |
| WO | WO 2006-003853 | 1/2006 | |
| WO | WO 2007-084266 | 7/2007 | |
| WO | WO 2009-032815 | 3/2009 | |
| WO | WO 2010-056541 | 5/2010 | |
| WO | WO 2010-056543 | 5/2010 | |
| WO | WO 2010-056544 | 5/2010 | |
| WO | WO 2010-124187 | 10/2010 | |
| WO | WO 2012-058605 | 5/2012 | |
| WO | WO 2012-083011 | 6/2012 | |
| WO | WO 2013-003373 | 1/2013 | |
| WO | WO 2013-096530 | 6/2013 | |
| WO | WO 2014-074336 | 5/2014 | |
| WO | WO 2014-151464 | 9/2014 | |
| WO | WO-2015134249 A1 * | 9/2015 | ............. C08L 33/06 |
| WO | WO 2016-100021 | 6/2016 | |
| WO | WO 2016-191235 | 12/2016 | |
| WO | WO 2016-191236 | 12/2016 | |
| WO | WO 2016-196914 | 12/2016 | |
| WO | WO 2019-195145 | 10/2019 | |
| WO | WO 2019-239286 | 12/2019 | |

OTHER PUBLICATIONS

Michielsen, "Specific Refractive Index Increments of Polymers in Dilute Solution," The Polymer Handbook, 2nd Edition Wiley-Interscience, (1999), p. VII / 548-593.

Podzimek, Light Scattering, Size Exclusion Chromatography and Asymmetric Flow Field Flow Fractionation: Powerful Tools for the Characterization of Polymers, Proteins and Nanoparticles, John Wiley & Sons, Inc., Hoboken, NJ, 2011, pp. 65-72.

International Search Report for PCT International Application No. PCT/IB2019/052727, dated Jul. 3, 2019, 4 pages.

International Search Report for PCT International Application No. PCT/US2019/025141, dated Jun. 17, 2019, 4 pages.

* cited by examiner

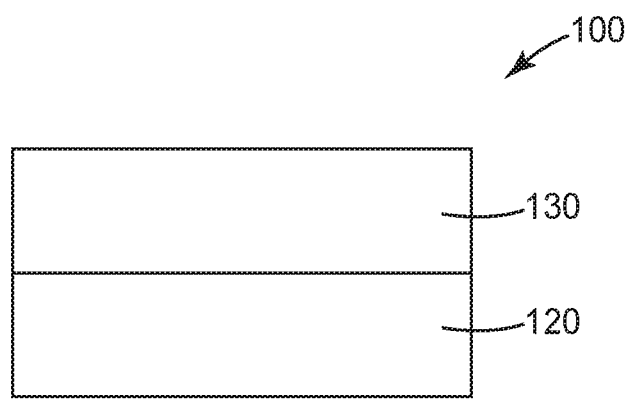

GEL ADHESIVE COMPRISING CROSSLINKED BLEND OF POLYDIORGANOSILOXANE AND ACRYLIC POLYMER

CROSS REFERENCE TO RELATED APPLICATIONS

This application is a national stage filing under 35 U.S.C. 371 of PCT/IB2019/052727, filed Apr. 3, 2019, which claims the benefit of U.S. Application No. 62/653,143, filed Apr. 5, 2018, the disclosure of which is incorporated by reference in its/their entirety herein.

BACKGROUND

A variety of gentle to skin articles and dressings have been described. For example, WO2010/056544 describes electron beam and gamma radiation crosslinked, silicone gel adhesives. Both nonfunctional and functional polydiorganosiloxanes are used. Methods of forming adhesive, and medical articles incorporating such adhesives are also described.

SUMMARY

Although various silicone gel adhesives have been described, it has been found that inclusion of certain acrylic polymers can be used to adjust the properties of a silicone gel adhesive. For example, in some embodiments the inclusion of acrylic polymers comprising polymerized units of polar monomer(s) can improve the (e.g. wet) adhesion. In other embodiments, the inclusion of acrylic polymers comprising polymerized units of high Tg monomer(s) can improve the cohesive strength.

In one embodiment, a method of making a silicone gel adhesive is described comprising providing an acrylic polymer, the acrylic polymer comprising at least 50 weight percent (wt.-%) of polymerized units of $C_1$-$C_{32}$ (meth)acrylate ester monomer and providing at least one non-functional polydiorganosiloxane, hydroxy-functional polydiorganosiloxane, or a mixture thereof. The method further comprises combining the acrylic polymer and polydiorganosiloxane into a mixture; coating the mixture onto a substrate, and subjecting the mixture to radiation thereby crosslinking the mixture.

In some embodiments, the non-functional polydimethylsiloxanes lack functional groups such that the non-functional polydimethylsiloxanes do not covalently bond with the acrylic polymer prior to subjecting the mixture to radiation.

In some embodiments, the hydroxy-functional polydimethylsiloxane(s) from covalent bond via condensation reactions and/or by reaction with the acrylic polymer.

The acrylic polymer is typically present in an amount ranging from 5 to 30 wt.-% of the adhesive. In some embodiments, the acrylic polymer comprises at least 50 wt.-% of polymerized units of $C_1$-$C_{32}$ (meth)acrylate ester monomer(s) wherein a homopolymer of said monomer(s) has a Tg no greater than 0° C. The acrylic polymer alone may be characterized as a pressure sensitive adhesive.

In typical embodiments, the silicone gel adhesive further comprises a silicate resin tackifier.

The step of combining the acrylic polymer and non-functional and/or hydroxy-functional polydiorganosiloxane typically comprises mixing, blending, milling, extrusion, or combinations thereof.

In some embodiments, the step of combining further comprises adding an organic solvent. In other embodiments, the step of combining is solventless (i.e. lacks an organic solvent).

Also described is a silicone gel adhesive comprising a crosslinked mixture of at least one non-functional polydiorganosiloxane, hydroxy-functional polydiorganosiloxane, or a mixture thereof; and an acrylic polymer comprising at least 50 wt.-% of polymerized units of alkyl (meth)acrylate monomers and a gel content of at least 20 wt.-%.

In other embodiments, medical articles or intermediates thereof are described comprising a layer of the silicone gel adhesive adhered to a substrate.

Also described are methods of use.

BRIEF DESCRIPTION OF THE DRAWINGS

FIG. 1 illustrates a medical article according to some embodiments of the present disclosure.

DETAILED DESCRIPTION

Presently described is a gel adhesive. "As used herein, the term "gel adhesive" refers to a tacky semi-solid crosslinked matrix containing a liquid or a fluid (inclusive of gums) that is capable of adhering to one or more substrates.

The silicone gel adhesive described here comprises at least one nonfunctional or hydroxy-functional polydiorganosiloxane, i.e., materials comprising a polysiloxane backbone that lacks functional groups that covalently bond with an acrylic polymer prior to subjecting the mixture to (e.g. electron beam or gamma) radiation.

In some embodiments, the nonfunctional silicone materials can be a linear material described by the following Formula 1 illustrating a siloxane backbone:

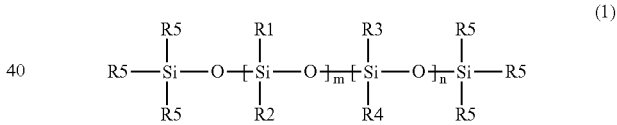

wherein R1, R2, R3, and R4 are independently selected from nonfunctional groups such as an alkyl group and an aryl group, each R5 is an alkyl group and n and m are integers, and at least one of m or n is not zero. In some embodiments, one or more of the alkyl or aryl groups may contain a halogen substituent, e.g., fluorine. For example, in some embodiments, one or more of the alkyl groups may be —$CH_2CH_2C_4F_9$.

In typical embodiments, R5 is a methyl group, i.e., the nonfunctional poly diorganosiloxane material is terminated by trimethylsiloxy groups. In some embodiments, R1 and R2 are alkyl groups and n is zero, i.e., the material is a poly(dialkylsiloxane). In some embodiments, the alkyl group is a methyl group, i.e., poly(dimethylsiloxane) ("PDMS"). In some embodiments, R1 is an alkyl group, R2 is an aryl group, and n is zero, i.e., the material is a poly(alkylarylsiloxane). In some embodiments, R1 is a methyl group and R2 is a phenyl group, i.e., the material is poly(methylphenylsiloxane). In some embodiments, R1 and R2 are alkyl groups and R3 and R4 are aryl groups, i.e., the material is a poly(dialkyldiarylsiloxane). In some embodiments, R1 and R2 are methyl groups, and R3 and R4 are phenyl groups, i.e., the material is poly(dimethyldiphenylsiloxane).

In some embodiments, the nonfunctional polydiorganosiloxane materials may be branched. For example, one or more of the R1, R2, R3, and/or R4 groups may be a linear or branched siloxane with alkyl or aryl (including halogenated alkyl or aryl) substituents and terminal R5 groups.

Thus, in typical embodiments the "nonfunctional groups" are either alkyl or aryl groups consisting of carbon, hydrogen, and in some embodiments, halogen (e.g., fluorine) atoms.

When the silicone gel is prepared from nonfunctional polydiorganosiloxane material(s), the silicone gel generally lacks functionalized polydiorganosiloxane materials that includes functional groups attached to the polysiloxane backbone that can form covalent bonds with the acrylic polymer of the gel adhesive. In the case of functionalized polydiorganosiloxane, one or more of the R groups of Formula 1 are functional groups such as hydrogen, hydroxy (including alkoxy); ethylenically unsaturated groups such as vinyl, allyl, or (meth)acrylate groups; or epoxy.

In other embodiments, the polydiorganosiloxane material is hydroxy functional. In this embodiment, a portion of the R5 groups of Formula 1 are —OH (i.e. hydroxy). At least a portion of the terminal group(s) are silanol groups having the formula —Si(R5) wherein at least one of the R5 groups is hydroxy. The other R5 groups are typically methyl. The hydroxy content of the silanol terminated polydiorganosiloxane can vary. In some embodiments, the hydroxyl content of the silanol terminated polydiorganosiloxane is at least 0.01, 0.02, or 0.03 wt.-%. In some embodiments, the hydroxyl content ranges up to 0.05, 0.06, 0.07, 0.08, 0.09 or 0.1 wt.-% of the silanol terminated polydiorganosiloxane. In other embodiments, the hydroxyl content is less than 0.01 wt.-% of the silanol terminated polydiorganosiloxane.

Silanol groups are subject to condensation reactions. Without intending to be bound by theory, such silanol groups may also react with (e.g. acidic groups of) the acrylic polymer.

Various mixtures of polydiorganosiloxanes can be utilized. In some embodiments, the silicone gel comprises a mixture of at least two non-functional polydiorganosiloxane (s). In some embodiments, the silicone gel comprises a mixture of at least two hydroxy-functional polydiorganosiloxane(s). In yet other embodiments, the mixture comprises at least one non-functional polydiorganosiloxane and at least one hydroxy-functional polydiorganosiloxane material.

The silicone gel adhesive is typically not formed by an addition cure reaction between vinyl-terminated poly(dimethylsiloxane) (PDMS) and hydrogen terminated PDMS, in the presence of a hydrosilation catalyst (e.g., platinum complex). Vinyl-terminated and hydrogen terminated PDMS chains are referred to as 'functionalized' silicones due to their specific chemical moieties. Individually, such functional silicones are generally not reactive; however, together they form a reactive silicone system. Thus, the silicone gel adhesive is free of hydrosilation catalyst (e.g., platinum complex).

In addition to the catalyst-promoted curing of silicone materials, it is known that free radicals formed from the high temperature degradation of organic peroxides can crosslink or cure silicone PSA formulations. This curing technique is undesirable due to the acidic residues left in the film from the curing chemistry, which are corrosive and unsuitable for skin contact. Thus, the silicone gel adhesive is also typically free of organic peroxides.

Generally, the non-functional and hydroxy-functional polydiorganosiloxanes may be characterized by their dynamic and/or kinematic viscosity. Useful polydiorganosiloxanes generally have a viscosity of at least 250 or 500 cST ranging up to 20 M (20,000,000) cST or greater.

Suitable non-functional and hydroxy-functional polydiorganosiloxanes are available from various supplies included Gelest, Wacker, Momentive, and Dow Corning. Illustrative non-functional and hydroxy-functional polydiorganosiloxanes are described in the following tables.

TABLE A

| Non-Functional and Hydroxy-Functional Polydiorganosiloxanes | |
|---|---|
| Trade Designation | Description |
| DMS-T25 | Trimethylsiloxy-terminated PDMS fluid with a viscosity of approximately 500 cSt available from Gelest (Morrisville, PA) |
| DMS-T35 | Trimethylsiloxy-terminated PDMS fluid with a viscosity of approximately 5,000 cSt available from Gelest (Morrisville, PA) |
| DMS-T43 | Trimethylsiloxy-terminated PDMS fluid with a viscosity of approximately 30,000 cSt available from Gelest (Morrisville, PA) |
| XIAMETER OHX-4070 Polymer 50000CS | Silanol terminated PDMS fluid with viscosity of 50,000 cSt available from Dow Corning (Midland, MI) |
| ELEMENT 14* PDMS 60K | A linear PDMS with a viscosity of approximately 60,000 cSt available from Momentive Performance Materials (US) |
| AK 60000 SILICONE FLUID | A linear non-reactive PDMS with a viscosity of approximately 60,000 cSt available from Wacker (Adrian, MI) |
| AK300000 SILICONE FLUID | A linear non-reactive PDMS with a viscosity of approximately 300,000 cSt available from Wacker (Adrian, MI) |
| AK500000 SILICONE FLUID | A linear non-reactive PDMS with a viscosity of approximately 500,000 cSt available from Wacker (Adrian, MI) |
| AK1000000 SILICONE FLUID | A linear non-reactive PDMS with a viscosity of approximately 1,000,000 cSt available from Wacker (Adrian, MI) |
| DMS-T72 | Trimethylsiloxy-terminated PDMS fluid with a viscosity of approximately 20,000,000 (20M) cSt available from Gelest (Morrisville, PA) |
| EL Polymer NA | Highly viscous nonfunctional PDMS gum available from Wacker (Adrian, MI) with a viscosity of approximately 10,000,000 (10M) cSt |

In some embodiments, the (e.g. hydroxy-functional) polydiorganosiloxanes have a dynamic and/or kinematic viscosity of at least 10,000; 20,000; 30,000; 40,000, or 50,000 cST or greater. In some embodiments, the (e.g. hydroxy-functional) polydiorganosiloxanes have a dynamic and/or kinematic viscosity of no greater than 100,000 cST.

In other embodiments, the (e.g. non-functional) polydiorganosiloxanes have a dynamic and/or kinematic viscosity of greater than 100,000 cST; such as at least 150,000; 200,000; 250,000; 300,000; 350,000; 400,000, 450,000 or 500,000 cST. In some embodiments, the (e.g. non-functional) polydiorganosiloxanes have a dynamic and/or kinematic viscosity ranging up to 1.5 M (1,500,000); 2 M; 2.5 M; 3 M; 3.5 M; 4 M; 4.5 M or 5 M cST. In some embodiments, the (e.g. non-functional) polydiorganosiloxanes have a dynamic and/or kinematic viscosity greater than 5 M cST ranging up to 10 M; or 15 M cST. In some embodiments, the (e.g. non-functional) polydiorganosiloxanes have a dynamic and/or kinematic viscosity greater than 15 M cST ranging up to 20 M cST or greater.

In some embodiments, a (e.g. non-functional) polydiorganosiloxanes having a viscosity of at least 500,000; 750,000; or 1 M cST or greater is combined with a lower viscosity (e.g. non-functional) polydiorganosiloxanes. The lower viscosity (e.g. non-functional) polydiorganosiloxanes typically has a viscosity of at least 250 or 500 cST ranging up to 100,000 cST.

The silicone gel adhesives are prepared by combining at least one acrylic polymer with one or more non-functional and/or hydroxy-functional polydiorganosiloxane material, coating the resulting combination (e.g. mixture) onto a substrate (e.g. backing) and crosslinking the mixture using electron beam (E-beam) or gamma irradiation.

In some embodiments, the non-functional and/or hydroxy-functional polydiorganosiloxane material and/or gel adhesives may include any of a variety of known additives including, but not limited to, tackifiers (e.g., MQ resins), fillers, pigments, additives for improving adhesion, additives for improving moisture-vapor transmission rate, pharmaceutical agents, cosmetic agents, natural extracts, silicone waxes, silicone polyethers, hydrophilic polymers and rheology modifiers.

In typical embodiments, the non-functional and/or hydroxy-functional polydiorganosiloxane material and silicone gel adhesive composition further comprise at least one silicate tackifying resin. Suitable silicate tackifying resins include those resins composed of the following structural units M (i.e., monovalent $R'_3SiO_{1/2}$ units), D (i.e., divalent $R'_2SiO_{2/2}$ units), T (i.e., trivalent $R'SiO_{3/2}$ units), and Q (i.e., quaternary $SiO_{4/2}$ units), and combinations thereof. Typical exemplary silicate resins include MQ silicate tackifying resins, MQD silicate tackifying resins, and MQT silicate tackifying resins. These silicate tackifying resins usually have a number average molecular weight in the range of 100 to 50,000 gm/mole, e.g., 500 to 15,000 gm/mole and generally R' groups are methyl groups.

MQ silicate tackifying resins are copolymeric resins where each M unit is bonded to a Q unit, and each Q unit is bonded to at least one other Q unit. Some of the Q units are bonded to only other Q units. However, some Q units are bonded to hydroxyl radicals resulting in $HOSiO_{3/2}$ units (i.e., "$T^{OH}$" units), thereby accounting for some silicon-bonded hydroxyl content of the silicate tackifying resin.

The level of silicon bonded hydroxyl groups (i.e., silanol) on the MQ resin may be reduced to no greater than 1.5 weight percent, no greater than 1.2 weight percent, no greater than 1.0 weight percent, or no greater than 0.8 weight percent based on the weight of the silicate tackifying resin. This may be accomplished, for example, by reacting hexamethyldisilazane with the silicate tackifying resin. Such a reaction may be catalyzed, for example, with trifluoroacetic acid. Alternatively, trimethylchlorosilane or trimethylsilylacetamide may be reacted with the silicate tackifying resin, a catalyst not being necessary in this case.

MQD silicone tackifying resins are terpolymers having M, Q and D units. In some embodiments, some of the methyl R' groups of the D units can be replaced with vinyl (CH2=CH—) groups ("$D^{Vi}$" units). MQT silicate tackifying resins are terpolymers having M, Q and T units.

Suitable silicate tackifying resins are commercially available from sources such as Dow Corning (MK1600, MQ1640), Momentive Performance Materials (e.g., SR545 and SR1000), and Wacker Chemie AG (e.g., BELSIL TMS-803).

In some embodiments, the weight ratio of non-functional and/or hydroxy-functional polydiorganosiloxane material to silicate tackifying resin ranges is at least 1:1, 1.1:1, 1.2:1, 1.3:1, 1.4:1, or 1.5. For example, the weight ratio may be characterized as 60/40, or in other words is 1.5:1. The weight ratio of non-functional and/or hydroxy-functional polydiorganosiloxane material to silicate tackifying resin can range up to 2:1, 3:1, 4:1, 5:1, 6:1, 7:1, 8:1, 9:1 or 10:1. The non-functional and/or hydroxy-functional polydiorganosiloxane material, the tackifying resin, when present, and any optional additives may be combined by any of a wide variety of known means prior to being coated and cured. For example, in some embodiments, the various components may be pre-blended using common equipment such as mixers, blenders, extruders, and the like. Typically, the polydiorganosiloxane material and tackifying resin, when present, are combined with each other forming a tackified silicone gel. This tackified silicone gel is then combined with an acrylic polymer.

The acrylic polymer comprises polymerized monomer units of a $C_1$-$C_{32}$ (meth)acrylate ester monomer (i.e., (meth) acrylic acid ester of a $C_1$-$C_{32}$ alkanol). Thus, the acrylic polymer is not a polyacrylic acid homopolymer. In some embodiments, these are $C_1$-$C_{24}$, $C_1$-$C_{18}$, or $C_1$-$C_{12}$ (meth) acrylate ester monomers. Examples of monomers suitable for use as the $C_1$-$C_{32}$ (meth)acrylate ester monomer include an ester of either acrylic acid or methacrylic acid with a non-tertiary alkanol such as ethanol, 1-propanol, 2-propanol, 1-butanol, 2-butanol, 1-pentanol, 2-pentanol, 3-pentanol, 2-methyl-1-butanol, 3-methyl-1-butanol, 1-hexanol, 2-hexanol, 2-methyl-1-pentanol, 3-methyl-1-pentanol, 2-ethyl-1-butanol, 3,5,5-trimethyl-1-hexanol, 3-heptanol, 1-octanol, 2-octanol, isooctylalcohol, 2-ethyl-1-hexanol, 1-decanol, 2-propylheptanol, 1-dodecanol, 1-tridecanol, 1-tetradecanol, citronellol, dihydrocitronellol, and the like.

In some embodiments it is desirable for the $C_1$-$C_{32}$ (meth)acrylate ester monomer to include a high Tg monomer, having a homopolymer Tg of at least 25° C., and preferably at least 50° C. Examples of suitable high Tg monomers useful in the present disclosure include, but are not limited to, t-butyl acrylate, methyl methacrylate, ethyl methacrylate, isopropyl methacrylate, n-butyl methacrylate, isobutyl methacrylate, s-butyl methacrylate, t-butyl methacrylate, stearyl methacrylate, phenyl methacrylate, cyclohexyl methacrylate, isobornyl acrylate, isobornyl methacrylate, benzyl methacrylate, 3,3,5-trimethylcyclohexyl acrylate, cyclohexyl acrylate, propyl methacrylate, and combinations thereof. The inclusion of high Tg monomer(s) can improve the cohesive strength of the silicone gel adhesive.

In some embodiments it is desirable for the $C_1$-$C_{32}$ (meth)acrylate ester monomer to include a low Tg monomer, having a homopolymer Tg less than 25° C., and preferably less than 0° C. In some embodiments, the low Tg monomer has a Tg no greater than −5° C., or no greater than −10° C. The Tg of these homopolymers is often greater than or equal to −80° C., greater than or equal to −70° C., greater than or equal to −60° C., or greater than or equal to −50° C.

Exemplary low Tg monomers include for example ethyl acrylate, n-propyl acrylate, n-butyl acrylate, isobutyl acrylate, n-pentyl acrylate, isoamyl acrylate, n-hexyl acrylate, 2-methylbutyl acrylate, 2-ethylhexyl acrylate, 4-methyl-2-pentyl acrylate, n-octyl acrylate, 2-octyl acrylate, isooctyl acrylate (Tg=−70° C.), isononyl acrylate, decyl acrylate, isodecyl acrylate, lauryl acrylate, isotridecyl acrylate, octadecyl acrylate, and dodecyl acrylate.

In some embodiments, the (e.g. pressure-sensitive adhesive) polymer comprises polymerized units of at least one low Tg monomer(s) having an alkyl group with at least 4 or 6 carbon atoms ranging up to 12, 18 or 24 carbon atoms. In some embodiments, the low Tg monomer has an alkyl group with 8 carbon atoms. Exemplary monomers include, but are not limited to, 2-ethylhexyl (meth)acrylate, isooctyl (meth) acrylate, n-octyl (meth)acrylate, 2-octyl (meth)acrylate, isodecyl (meth)acrylate, and lauryl (meth)acrylate.

In some embodiments, polymerized units of (e.g. low and/or high Tg) $C_1$-$C_{32}$ (meth)acrylate ester monomer(s) are present in an amount of at least 50 wt.-%, based on the total weight of the acrylic polymer. In some embodiments, the polymerized units of (e.g. low and/or high Tg) $C_1$-$C_{32}$ (meth)acrylate ester monomer(s) are present in an amount of at least 55, 60, 65, 70, 75, 80, 85, 95 wt.-% or greater based on the total weight of the acrylic polymer. The polymerized units of (e.g. low and/or high Tg) $C_1$-$C_{32}$ (meth)acrylate ester monomer(s) are present in an amount of at least 2.5, 5, 10, 15, 20, 25, or 30 wt.-% based on the total weight of the silicone gel adhesive. In some embodiments, the polymerized units of low Tg $C_1$-$C_{32}$ (meth)acrylate ester monomer(s) are of a sufficient concentration such that the resulting acrylic polymer in the absence of additives (e.g. tackifier, plasticizer) is a pressure sensitive adhesive according to the Dahlquist Criteria for Tack" that states a PSA has a shear storage modulus (G') of less than $3\times10^6$ dyne/$cm^2$ (0.3 MPa) at approximately room temperature (25° C.) and a frequency of 1 Hz.

The (e.g. pressure-sensitive adhesive) acrylic polymer, may further include polymerized units of an acid-functional monomer, wherein the acid-functional group may be an acid per se, such as a carboxylic acid, or a portion may be salt thereof, such as an alkali metal carboxylate. Useful acid-functional monomers include, but are not limited to, those selected from an ethylenically unsaturated carboxylic acid, ethylenically unsaturated sulfonic acid, ethylenically unsaturated phosphonic acid, and mixtures thereof. Examples of such compounds include those selected from acrylic acid, methacrylic acid, itaconic acid, fumaric acid, crotonic acid, citraconic acid, maleic acid, oleic acid, β-carboxyethyl (meth)acrylate, 2-sulfoethyl methacrylate, styrene sulfonic acid, 2-acrylamido-2-methylpropanesulfonic acid, vinylphosphonic acid, and mixtures thereof.

Due to their availability, an acid-functional monomer is generally selected from ethylenically unsaturated carboxylic acids (i.e., (meth)acrylic acids). When even stronger acids are desired, acidic monomers can include the ethylenically unsaturated sulfonic acids and ethylenically unsaturated phosphonic acids.

When present, the (e.g. pressure sensitive adhesive) acrylic polymer typically comprises polymerized units of an acid-functional, ethylenically unsaturated monomer(s) in an amount of at least 0.5, 1, 1.5, 2, 2.5, 3, 2.5, 4, 4.5, or 5 wt.-%, based on the total weight of the polymer. In some embodiments, the (e.g. pressure sensitive adhesive) polymer comprises polymerized units of an acid-functional, ethylenically unsaturated monomer(s) in an amount of up to 10, 15, 20, 25, 30, 35, 40, 45, or 50 wt.-%, based on the total weight of the acrylic polymer. The amount of polymerized units of an acid-functional, ethylenically unsaturated monomer(s) are present in an amount of at least 0.025, 0.05, 0.10, 0.15, 0.20, or 0.25 wt.-% ranging up to 0.5, 1, 2, 3, 4, 5, 5, 6, 8, 9, 10, 11, 12, 13, 14, or 15 wt.-%, based on the total weight of the silicone gel adhesive.

The acid-functional groups of the acrylic polymer can covalently bond with the hydroxy functional groups of the hydroxy-functional polydiorganosiloxane material(s).

The (e.g. pressure sensitive adhesive) polymers may further comprise polymerized units of a polar monomer. As used herein, the term "polar monomer" is exclusive of acid-functionality and is referred to as a "non-acid-functional, ethylenically unsaturated polar monomer."

Representative examples of suitable such polar monomers include, but are not limited to, 2-hydroxyethyl (meth)acrylate; 4-hydroxybutyl (meth)acrylate; N-vinylpyrrolidone; N-vinylcaprolactam; acrylamide; mono- or di-N-alkyl substituted acrylamide; t-butyl acrylamide; dimethylaminoethyl acrylamide; N-octyl acrylamide; a poly(alkoxyalkyl) (meth) acrylate including 2-(2-ethoxyethoxy)ethyl (meth)acrylate, 2-ethoxyethyl (meth)acrylate, 2-methoxyethoxyethyl (meth) acrylate, 2-methoxyethyl methacrylate, and a polyethylene glycol mono(meth)acrylate; an alkyl vinyl ether, including vinyl methyl ether; and mixtures thereof. When the acrylic polymer comprises polymerized units of polar monomers, such polyethylene glycol (PEG) mono(meth)acrylate, the gel adhesive can exhibit improved adhesion to wet surfaces. In some embodiments, homopolymers of such polar monomers are typically not compatible with the polydiorganosiloxane material, particularly at higher concentrations. However, the presence of the polymerized units of the $C_1$-$C_{32}$ (meth)acrylate ester monomer(s) of the acrylic copolymer is surmised to aid in the compatibility with the non-functional and/or hydroxy-functional polydiorganosiloxane material.

In some embodiments, the (e.g. pressure sensitive adhesive) acrylic polymer comprises polymerized units of a non-acid ethylenically unsaturated polar monomer(s) in an amount of at least 0.5, 1, 1.5, 2, 2.5, 3, 2.5, 4, 4.5, or 5 wt.-%, based on the total weight of the polymer. In some embodiments, the (e.g. pressure sensitive adhesive) polymer comprises polymerized units of a non-acid ethylenically unsaturated polar monomer(s) in an amount of up to 10, 15, 20, 25, 30, 35, 40, 45, or 50 wt.-%, based on the total weight of the polymer. The amount of polymerized units of non-acid ethylenically unsaturated polar monomer(s) are present in an amount of at least 0.025, 0.05, 0.10, 0.15, 0.20, or 0.25 wt.-% ranging up to 0.5, 1, 2, 3, 4, 5, 5, 6, 8, 9, 10, 11, 12, 13, 14, or 15 wt.-%, based on the total weight of the silicone gel adhesive. In other embodiments, polymerized units of a non-acid ethylenically unsaturated polar monomer(s) are not present in the acrylic copolymer.

The acrylic (e.g. pressure-sensitive adhesive) polymers, may further include one or more other vinyl monomers. When used, vinyl monomers useful in the (meth)acrylate polymer include a vinyl ester (e.g., vinyl acetate and vinyl propionate), styrene, substituted styrene (e.g., α-methyl styrene), vinyl halide, and mixtures thereof. As used herein vinyl monomers are exclusive of acid-functional monomers, acrylate ester monomers, and polar monomers.

When present, the (e.g. pressure sensitive adhesive) polymer typically comprises polymerized units of vinyl monomer(s) in an amount of at least 0.5 or 1 ranging up to 5 wt.-%, based on the total weight of the acrylic polymer.

In some embodiments, the inclusion of the acrylic polymer improves the dry or wet 180 degree adhesion, as compared to the same silicone adhesive gel lacking such acrylic polymer. The dry and wet 180 degree peel adhesion can be determined according to the test methods described in the examples. In one embodiment, the silicone adhesive gel lacking such acrylic polymer has an average dry and wet 180 degree peel adhesion of about 6-8 ounces/inch. However, the inclusion of the acrylic polymer can raise the average dry and/or wet 180 degree peel adhesion to at least 10, 11, 12, or 13 ounces per inch. In another embodiment, the silicone adhesive gel lacking such acrylic polymer has an average dry and wet 180 degree peel adhesion of about 9-16 ounces/inch. However, the inclusion of the acrylic polymer can raise the average dry and/or wet 180 degree peel adhesion to at least 18, 19, or 20 ounces per inch. In another embodiment, the silicone adhesive gel lacking such acrylic polymer has an average dry and wet 180 degree peel adhesion of about 11-13 ounces/inch. However, the inclusion of the acrylic polymer can raise the average dry and/or wet 180 degree peel adhesion to at least 15, 16, 17, 18, 19, 20, 21, 22, 23, 24, 25, 26 or 27 ounces per inch.

In yet other embodiment, inclusion of the acrylic polymer reduces the cost of the silicone gel adhesive. In this embodiment, the silicone gel adhesive comprising acrylic polymer may have comparable properties to the (e.g. same) silicone gel adhesive lacking acrylic polymer.

The (e.g. pressure-sensitive adhesive) polymers, described herein may be prepared by a variety of conventional free radical polymerization methods, including solution, radiation, bulk, dispersion, emulsion, and suspension processes. The monomer mixture may comprise a polymerization initiator, especially a thermal initiator or a photoinitiator of a type and in an amount effective to polymerize the monomers, as described below. For optical applications, solution, UV, and bulk processes are preferred. Other processes may introduce birefringence or foreign materials that may affect optic properties. The resulting adhesive copolymers of the present disclosure may be random or block copolymers.

The acrylic polymers may be prepared via suspension polymerizations as disclosed in U.S. Pat. No. 3,691,140 (Silver); U.S. Pat. No. 4,166,152 (Baker et al.); U.S. Pat. No. 4,636,432 (Shibano et al); U.S. Pat. No. 4,656,218 (Kinoshita); and U.S. Pat. No. 5,045,569 (Delgado).

Initiators useful in preparing the (meth)acrylate polymers of the present disclosure are initiators that, on exposure to heat, generate free-radicals which initiate (co)polymerization of the monomer mixture. Suitable initiators include, but are not limited to, those selected from the group consisting of potassium persulfate, ammonium persulfate, sodium persulfate, and mixtures thereof; an oxidation-reduction initiator such as the reaction product of an above-mentioned persulfate and a reducing agent such as those selected from the group consisting of sodium metabisulfite and sodium bisulfite; and 4,4'-azobis(4-cyanopentanoic acid) and its soluble salts (e.g., sodium, potassium). The preferred water-soluble initiator is potassium persulfate. Suitable oil-soluble initiators include, but are not limited to, those selected from the group consisting of an azo compound such as VAZO 64 (2,2'-azobis(isobutyronitrile)) and VAZO 52 (2,2'-azobis(2,4-dimethylpentanenitrile)) (both available from E.I. du Pont de Nemours Co.), peroxides such as benzoyl peroxide and lauroyl peroxide, and mixtures thereof. The preferred oil-soluble thermal initiator is (2,2'-azobis(isobutyronitrile)). When used, initiators may be included in an amount up to 1 parts by weight, preferably from 0.05 to 1 parts by weight, more preferably 0.1 to 0.5 parts by weight, relative to 100 parts by weight of total monomer.

The polymerizable mixture may optionally further comprise chain transfer agents to control the molecular weight of the resultant polymer. Examples of useful chain transfer agents include, but are not limited to, those selected from the group consisting of carbon tetrabromide, alcohols, mercaptans, and mixtures thereof. When present, the preferred chain transfer agents are isooctylthioglycolate, tertiary dodecyl mercaptan, and carbon tetrabromide. If used, the polymerizable mixture may include up to 1 parts by weight of a chain transfer agent, typically 0.01 parts by weight to 0.5 parts by weight, and more typically 0.05 parts by weight to 0.2 parts by weight, relative to 100 parts by weight of the total monomer.

A typical solution polymerization method is carried out by adding the monomers, a suitable solvent, and an optional chain transfer agent to a reaction vessel, adding a free radical initiator, purging with nitrogen, and maintaining the reaction vessel at an elevated temperature, typically in the range of 40 to 100° C. until the reaction is completed, typically in 1 to 20 hours, depending upon the batch size and temperature. Examples of the solvent are methanol, tetrahydrofuran, ethanol, isopropanol, acetone, methyl ethyl ketone, methyl acetate, ethyl acetate, toluene, xylene, and ethylene glycol alkyl ether. Those solvents can be used alone or as mixtures thereof.

In a typical photopolymerization method, a monomer mixture may be irradiated with ultraviolet (UV) rays in the presence of a photopolymerization initiator (i.e., photoinitiators). Preferred photoinitiators are those available under the trade designations OMNIRAD from IGM Resins, USA and include 1-hydroxy cyclohexyl phenyl ketone (OMNIRAD 184), 2,2-dimethoxy-1,2-diphenylethan-1-one (OMNIRAD 651), bis(2,4,6-trimethylbenzoyl)phenylphosphineoxide (OMNIRAD 819), 1-[4-2-hydroxyethoxy)phenyl]-2-hydroxy-2-methyl-1-propane-1-one (OMNIRAD 2959), 2-benzyl-2-dimethylamino-1-(4-morpholinophenyl)butanone (OMNIRAD 369), 2-methyl-1-[4-(methylthio)phenyl]-2-morpholinopropan-1-one (OMNIRAD 907), and 2-hydroxy-2-methyl-1-phenyl propan-1-one (OMNIRAD 1173). Particularly preferred photoinitiators are OMNIRAD 819, 651, 184 and 2959.

Solventless polymerization methods may also be utilized to prepare the acrylic polymers, such as the continuous free radical polymerization method described in U.S. Pat. No. 4,619,979 (Kotnour et al.) and U.S. Pat. No. 4,843,134 (Kotnour et al.), the essentially adiabatic polymerization methods using a batch reactor described in U.S. Pat. No. 5,637,646 (Ellis), and the methods described for polymerizing packaged pre-adhesive compositions described in U.S. Pat. No. 5,804,610 (Hamer et al.).

The molecular weight of the (e.g. pressure-sensitive adhesive) acrylic polymer can vary depending on the polymerization technique. The inherent viscosity, as determined by the test method described in the examples, is indicative of molecular weight. In some embodiments, the inherent viscosity of the acrylic polymer is at least 0.4 or 0.5. In some embodiments, the inherent viscosity of the acrylic polymer ranges up to 0.9 or greater. The molecular weight of the polymer can be increased by chemical or radiant energy crosslinking.

In some embodiments, the acrylic polymer may be crosslinked prior to combining the acrylic polymer with the non-functional and/or hydroxy-functional polydiorganosiloxane material.

There are several crosslinking mechanisms for acrylic polymers (particularly, adhesives) including free-radical copolymerization of multifunctional, ethylenically unsaturated groups with the other monomers, and covalent or ionic crosslinking through the functional monomers, such as acrylic acid. Another method is the use of UV crosslinkers, such as copolymerizable benzophenones or post-added photocrosslinkers, such as multifunctional benzophenones and triazines. In the past, a variety of different materials have been used as crosslinking agents, e.g., polyfunctional acrylates, acetophenones, benzophenones, and triazines. Crosslinking may also be achieved using high energy electromagnetic radiation such as gamma or e-beam radiation. In this case, no additional crosslinker may be required. One or more of these mechanisms can be used with the polymers described herein.

In order to increase cohesive strength of the coated (particularly, adhesive) composition, a multifunctional (meth)acrylate may be incorporated into the blend of polymerizable monomers. A multifunctional (meth)acrylate is particularly useful for emulsion or syrup polymerization. Examples of a useful multifunctional (meth)acrylate include, but are not limited to, a di(meth)acrylate, tri(meth)acrylate, and tetra(meth)acrylate, such as 1,6-hexanediol di(meth)acrylate, a poly(ethylene glycol) di(meth)acrylate, polybutadiene di(meth)acrylate, a polyurethane di(meth)acrylate, propoxylated glycerin tri(meth)acrylate, and mixtures thereof.

When present, the (e.g. pressure sensitive adhesive) acrylic polymer typically comprises polymerized units of multifunctional (meth)acrylate monomer(s) in an amount of at least 0.01, 0.02, 0.03, 0.04, or 0.05 ranging up to 1, 2, 3, 4, or 5 wt.-%, based on the total weight of the polymer.

The (e.g. pressure-sensitive adhesive) acrylic polymer may optionally comprise one or more conventional additives such as tackifiers, plasticizers, dyes, antioxidants, and UV stabilizers. Suitable antioxidants for acrylic polymer are known, some of which are described in U.S. Pat. No. 7,968,661 (Ellis and Stark); incorporated herein by reference.

In one embodiment, a method of making a silicone gel adhesive composition is described comprising providing an acrylic polymer, the acrylic polymer comprising at least 50 wt.-% of polymerized units of $C_1$-$C_{32}$ (meth)acrylate ester monomer as previously described; providing a non-functional and/or hydroxy-functional polydiorganosiloxane material; combining the acrylic polymer and polydiorganosiloxane material(s) into a mixture; coating the mixture onto a substrate, and subjecting the mixture to radiation thereby crosslinking the mixture.

The amount of acrylic polymer that is combined with the polydiorganosiloxane material(s) is typically at least 1, 2, 3, 4, or 5 wt.-% based on the total weight of the gel adhesive. In typical embodiments, the amount of acrylic polymer is no greater than 30, 29, 28, 27, 26, 25, 24, 23, 22, 21 or 20 wt.-% based on the total weight of the silicone gel adhesive. When the concentration of acrylic polymer is too low, the benefit obtained from adding the acrylic polymer, such as improved adhesion, may be insignificant. When the concentration of acrylic polymer is too high, the mixture may exhibit cohesive failure when subjected to the 180 degree peel test to stainless steel (as further described in the examples).

In some embodiments, the mixture of non-functional and/or hydroxy-functional polydiorganosiloxane material(s), acrylic polymer, and preferably silicate tackifying resin may be dissolved in a solvent, coated, and dried prior to curing. In some embodiments, solventless compounding and coating processes may be used. In some embodiments, solventless coating may occur at about room temperature. For example, in some embodiments, the materials may have kinematic viscosity of no greater than 100,000 centistokes (cSt), e.g., no greater than 50,000 cSt. However, in some embodiments, hot melt coating processes such as extrusion may be used, e.g., to reduce the viscosity of higher molecular weight materials to values more suitable for coating. The various components may be added together, in various combinations or individually, through one or more separate ports of an extruder, blended (e.g., melt mixed) within the extruder, and extruded to form the hot melt coated composition.

Regardless of how it is formed, the method comprising subjecting the (e.g. coated) mixture to radiation thereby crosslinking the mixture. Exposure to electron beam (e-beam) or gamma radiation generates free radicals. Therefore, non-functional siloxane materials are curable in this way and no initiators or catalysts are required, as described, for example, in PCT Publication Nos. WO 2010/056541 and 2010/056543 (Liu et al.).

Prior to such radiation curing, the mixture is substantially free of crosslinking such that the mixture dissolves in ethyl acetate at a concentration of 30 mg/g of ethyl acetate at ambient temperature (25° C.). The (e.g. radiation) crosslinked mixture (i.e. silicone gel adhesive) has a gel content (as determined by the method described in the examples) of at least 20, 25, 30, 35, 40, 45 or 50 wt.-%. In some embodiments, the (e.g. radiation) crosslinked mixture has a gel content of at least 55, 60, 65, 70, 75, or 80 wt.-%.

A variety of processes and equipment for E-beam and gamma ray curing are well-known. The cure depends on the specific equipment used, and those skilled in the art can define a dose calibration model for the specific equipment, geometry, and line speed, as well as other well understood process parameters. The level of crosslinking desired can be controlled by controlling the dose of E-beam or gamma ray radiation used.

The dose of (e.g. E-beam and gamma ray) curing is typically at least 0.25 or 0.5 Mrads and may range up to 7.5 Mrads or greater. The dose can vary depending on the dynamic and/or kinematic viscosity of the non-functional and/or hydroxy-functional polydiorganosiloxane(s) and extent of crosslinking desired. For example, when the (e.g. non-functional) polydiorganosiloxane has a very high molecular weight (e.g. 10 M cST viscosity), a dose of 0.5 Mrads can be suitable. However, for lower molecular weights (e.g. less than 100,000 cST viscosity), doses as high as 7.3 Mrads can be suitable. In the case of a 1 M viscosity (e.g. non-functional) polydiorganosiloxane, doses greater than 2.4 Mrad can be preferred to prevent residue when subjected to 180 degree peel testing to stainless steel. Various intermediate doses can be utilized.

Commercially available electron beam generating equipment is readily available. For the examples described herein, the radiation processing was performed on a Model CB-300 electron beam generating apparatus (available from Energy Sciences, Inc. (Wilmington, MA). Generally, a support film (e.g., polyester terephthalate support film) runs through a chamber. In some embodiments, a sample of the uncured material may be applied to a substrate (e.g. backing) attached to the support film and conveyed at a fixed speed of about 6.1 meters/min (20 feet/min). Generally, the chamber is inerted (e.g., the oxygen-containing room air is replaced with an inert gas, e.g., nitrogen) while the samples are e-beam cured, particularly when open-face curing.

The exposed side of the uncured material may be exposed to E-beam irradiation. For making a single layer laminating adhesive type tape, a single pass through the electron beam may be sufficient. Thicker samples, may exhibit a cure gradient through the cross section of the adhesive so that it may be desirable to expose the uncured material to electron beam radiation from both sides.

Commercially available gamma irradiation equipment includes equipment often used for gamma irradiation sterilization of products for medical applications. In some embodiments, such equipment may be used to cure, or partially cure the gentle to skin adhesives described herein. In some embodiments, such curing may occur simultaneously with a sterilization process for a semi-finished or finished product, for example a tape or wound dressing.

Silicone gel adhesives, as described herein, have excellent wetting characteristics, due to the very low glass transition temperature (Tg) and modulus of the polysiloxane network. Rheologically, these gels exhibit similar storage moduli at bond making and bond breaking time scales, resulting in relatively low to moderate forces being required to debond the adhesive by peeling. This results in minimal to no skin trauma upon removal. Additionally, the elastic nature of the crosslinked gel prevents flow of the adhesive around hair during skin wear, further reducing the instances of pain during removal.

In some embodiments, the (e.g. gentle to skin) adhesives are suitable for forming medical articles such as tapes, wound dressings, electrodes, surgical drapes, IV site dressings, a prosthesis, an ostomy or stoma pouch, a buccal patch, or a transdermal patch. In some embodiments, the adhesives may also be useful for other medical articles including dentures and hairpieces.

In some embodiments, the (e.g. gentle to skin) adhesives are suitable for adhering a medical substrate to a biological material. For example, in some embodiments, the gentle to skin adhesives may be used to adhere medical articles to the skin of humans and/or animals. In some embodiments, the average peel adhesion to a biological surface (e.g. human) skin may be less than 200 gm/2.54 cm, and in some embodiments, less than 100 gm/2.54 cm.

Exemplary medical article 100 is illustrated in FIG. 1. Medical article 100 comprises the silicone gel adhesive described herein 130 associated with a first major surface of substrate 120. Although not shown, in some embodiments, the opposite surface adhesive 130 may be protected by a release liner.

A wide variety of substrates are suitable for the medical articles described herein. In many embodiments, the substrate comprises a substrate suitable for use in a medical article. Examples of suitable substrates include a polymeric film, a fabric, a non-woven, a foam, a paper, a mesh, an adhesive, or a release liner. In some embodiments, the breathable conformable backing comprises a high moisture vapor permeable film backing. Examples of such backings, methods of making such films, and methods for testing their permeability are described, for example, in U.S. Pat. Nos. 3,645,835 and 4,595,001.

Generally, the backing is conformable to anatomical surfaces. As such, when the backing is applied to an anatomical surface, it conforms to the surface even when the surface is moved. Generally, the backing is also conformable to animal anatomical joints. When the joint is flexed and then returned to its unflexed position, the backing stretches to accommodate the flexion of the joint, but is resilient enough to continue to conform to the joint when the joint is returned to its unflexed condition.

Examples of particularly suitable backings can be found in U.S. Pat. Nos. 5,088,483 and 5,160,315, and include elastomeric polyurethane, polyester, or polyether block amide films. These films have a combination of desirable properties including resiliency, high moisture vapor permeability, and transparency.

A combination of substrate layers can also be used. For example, a backing substrate can used in conjunction with a release liner, such that one surface of the gel adhesive is in contact with the backing substrate, and the other is contact with a release liner. Other combinations can also be used.

In some embodiments, it may be desirable for there to be a primer layer between the substrate surface and the gel adhesive layer. Generally, the primer layer comprises materials that are commonly referred to as "primers" or "adhesion promoters". Primers and adhesion promoters are materials that are applied as thin coatings on a surface and strongly adhere to the surface and provide a modified surface chemistry to the surface. Examples of suitable coating materials include polyamides, poly(meth)acrylates, chlorinated polyolefins, rubbers, chlorinated rubbers, polyurethanes, siloxanes, silanes, polyester, epoxies, polycarbodiimides, phenolics, and combinations thereof.

The primer layer may be applied to the substrate as a solventborne mixture, a waterborne mixture, or as a 100% solids composition. Typically, the primer layer is applied as a solventborne or a waterborne mixture.

Examples of suitable commercially available primer layer materials include: the polyamide UNI-REZ available from Arizona Chemical; the polyacrylate RHOPLEX from Dow Chemical; the chlorinated polyolefins such as EASTMAN CP-343 available from Eastman Chemical, or SUPERCHLON from Nippon Paper Chemicals; the synthetic rubber KRATON materials available from Kraton Polymers; the polyurethane NEO-REZ available from DSM; the siloxanes described in U.S. Pat. No. 5,866,222 (Seth et al.) and U.S. patent application Ser. No. 61/579,115 filed on Dec. 22, 2011, titled "Adhesive Article Including Primer Layer and Method of Making the Same"; the SILQUEST silane materials available from Momentive; the polyester EASTMAN AQ resins available from Eastman Chemical; the epoxy DER materials available from Dow Chemical; the polycarbodiimides described in U.S. Pat. No. 4,060,664; and the phenolic BKS resins from Georgia-Pacific.

In some embodiments, the primer layer composition comprises a film-forming resin and may additionally contain a wide variety of additional additives. The selection of the film forming resin or resins is affected by an array of properties including solubility of the resin, and the molecular weight and Tg of the polymer of polymers in the resin.

Various film-forming resins are known. Representative film-forming resins include acrylic resin(s), polyvinyl resin(s), polyester(s), polyacrylate(s), polyurethane(s) and mixtures thereof. Polyester resins include copolyester resins commercially available from Bostik Inc., Middleton, Mass. under the trade designation "VITEL 2300BG"; copolyester resins available from Eastman Chemical, Kingsport, Tenn. under the trade designation "EASTAR"; copolyester resins from DSM, Heerlen, the Netherlands, under the trade designation "ARNITEL"; as well as other polyester resins available from Bayer, Pittsburg, Pa. under the trade designations "MULTRON" and "DESMOPHEN"; Spectrum Alkyd & Resins Ltd., Mumbia, Maharshtra, India under the trade designation "SPECTRAALKYD" and Akzo Nobel, Chicago, Ill. under the trade designation "SETALIN" alkyd.

Solvent-based primer compositions comprise the base polymer admixed with a solvent. The solvent may be a single solvent or a blend of solvents. The solvent-based primer composition generally contains about 5 to about 60 parts by weight of the base polymer, more typically about 10 to about 40 parts base polymer or even about 10 to about 30 parts base polymer, with the remainder of the primer composition being solvent and optional additives.

Among the particularly suitable film forming resins are silicone copolymers such as those described in U.S. Pat. No. 9,890,302 (Tse et al.). Acrylic resins, polyvinyl resins and mixtures thereof are also suitable. Various acrylic resins are known. In general, acrylic resins are prepared from various (meth)acrylate monomers such as polymethylmethacrylate (PMMA), methyl methacrylate (MMA), ethyl acrylate (EA), butyl acrylate(BA), butyl methacrylate (BMA), n-butyl methacrylate (n-BMA) isobutylmethacrylate (IBMA), polyethylmethacrylate (PEMA), etc. alone or in combination with each other. Exemplary acrylic resins include those commercially available from Rohm and Haas, Co., Philadelphia, Pa. under the trade designation "PARALOID" and from Ineos Acrylics, Cordova, Tenn. under the trade designation "ELVACITE" resins. Other suitable polyacrylic materials include those from S. C. Johnson, Racine, Wis. under the trade designation "JONCRYL" acrylics. Polyvinyl resins include vinyl chloride/vinyl acetate copolymers, such as those available from Rohm and Haas, Co., Philadelphia, Pa. under the trade designation "ACRYLOID" and those available from Union Carbide Corp., a subsidiary of The Dow Chemical Company ("Dow"), Midland Mich. under the trade designation "VYHH" as well as vinyl chloride/vinyl acetate/vinyl alcohol terpolymers also commercially available from Union Carbide Corp. under the trade designation "UCAR VAGH". Other polyvinyl chloride resins are available from Occidental Chemical, Los Angeles, Calif.; BF Goodrich Performance Materials, Cleveland, Ohio; and BASF, Mount Olive, NJ. In some embodiments, UV cured (meth)acrylate coatings may also be used as a primer coating as described in PCT Publication No. WO 2016/100,021 (Kluge et al.).

Suitable water-based primers are generally emulsions or dispersions that are substantially free of water soluble base polymers as a major component. Water-based emulsions and dispersions are advantageous to reduce solvent emissions by employing primer compositions that are substantially free of volatile organic solvents. An exemplary water-based primer includes a crosslinked poly(meth)acrylate polymer such as a butyl acrylate/methyl methacrylate copolymer crosslinked with a sulfo-urethane-silanol polymer.

In some embodiments, it may be desirable that the second major surface of the substrate, that is to say the surface on which the gel adhesive is not coated, have a low adhesion coating. This is especially true if the gel adhesive article is to be supplied in the form of a tape. Many tapes are supplied as rolls, where the adhesive layer contacts the non-adhesive "back" side of the backing upon being rolled up. Often this non-adhesive surface of the backing has a low adhesion or release coating on it to permit the roll to be unwound. These low adhesion coatings are often called "low adhesion backsizes" or LABs. Many factors control whether an LAB coating is necessary or desirable, including the nature of the adhesive, the composition and topography of the backing, and the desired use for the tape article. For example, some polyolefinic backings have a sufficiently low surface energy that an LAB coating is not required when used with some classes of pressure sensitive adhesives.

LAB coatings are widely used in the adhesive arts. Typically, the use of LABs have proven useful, especially in tape applications. For some tape uses, the presence of LABs can be detrimental. For example, masking tapes are often used to mask areas to be painted. Upon completion of the painting, the masking tape is removed. In some instances, when LAB coatings are used on the masking tape, the paint does not adhere well to the LAB coated surface and can run or flake off to contaminate the painted surface.

Similarly, a variety of tapes are designed to wrap upon themselves in use. Examples of these types of tapes are athletic tapes, duct tapes, electrical tapes, as well as a variety of medical tapes. With these tapes, the LAB coating must provide sufficiently easy release to permit facile unwinding of the tape, and yet must adhere sufficiently strongly to the adhesive to permit the tape to wrap upon itself and retain the adhesion throughout the period of use of the tape.

The gel adhesive may be of any suitable thickness, from quite thin to quite thick. In some embodiments, the thickness will be at least 10 micrometers (0.5 mil), up to 305 micrometers (12 mils), and in some embodiments the thickness will be from 25 micrometers (1 mil) up to 152 micrometers (6 mils), or even from 25 micrometers (1 mil) up to 102 micrometers (4 mils) thick. In some embodiments, the thickness may range up to 150, 200, 250, 300, 350, or 400 micrometers. A wide range of intermediate thicknesses are also suitable.

The gel adhesive layer may be a continuous layer, or it may be a discontinuous layer. For example, the gel adhesive layer may be stripe coated such that stripes of gel adhesive are present on the first major surface of the substrate. In other embodiments, the gel adhesive may have through holes. Through holes are holes that pass through the entire thickness of the adhesive layer.

EXAMPLES

Unless otherwise noted, all parts, percentages, ratios, etc. in the Examples and the rest of the specification are by weight. Unless otherwise indicated, all other reagents were obtained, or are available from fine chemical vendors such as Sigma-Aldrich Company, St. Louis, Mo., or may be synthesized by known methods. Table 1 (below) lists materials used in the examples and their sources. In the following tables, ACRYLIC POLYM=acrylic polymer; IV=intrinsic viscosity; NM=not measured; and N/A=not applicable.

TABLE 1

Materials List

| DESIGNATION | DESCRIPTION | SOURCE |
|---|---|---|
| IOA | Isooctyl acrylate | 3M (Maplewood, MN, USA) |
| PEG | PEG-acrylate in isooctyl acrylate | 3M |
| AA | Acrylic acid | BASF (Ludwigshafen, Germany) |

TABLE 1-continued

Materials List

| DESIGNATION | DESCRIPTION | SOURCE |
|---|---|---|
| IOTG | Isooctyl thioglycolate | Evans Chemetics LP (Teaneck, NJ, USA) |
| AeBP | Acryloxyethoxy benzophenone | 3M |
| V67 | 2,2'-azobis(2-methylbutyronitrile) obtained under the trade designation VAZO 67 | E. I. du Pont de Nemours and Company (Wilmington, DE, USA) |
| Ethyl acetate | Ethyl acetate | Honeywell (Morris Plains, NJ, USA) |
| AK1000K | A linear, non-reactive polydimethylsiloxane fluid obtained under the trade designation WACKER AK 1000000 SILICONE FLUID (viscosity, kinematic at 25° C. is approximately 1000000 mm$^2$/s) | Wacker Chemie AG (Munich, Germany) |
| OHX-4070 | A polydimethylsiloxane fluid that is hydroxy terminated and has a dynamic viscosity of 50000 cP | Xiameter (Midland, MI, USA) |
| 803TF | An MQ silicate resin (co-hydrolysis product of tetraalkoxy silane (Q unit) and trimethyl-ethoxy silane (M unit)) obtained under the trade designation MQ-RESIN POWDER 803 TF | Wacker Chemie AG |
| Backing | A backing film was provided by extruding a thermoplastic polyester elastomer onto a nonwoven polyester material, wherein the elastomer material had a three second Shore D hardness of 32 as tested per ISO 868 and a melting temperature of approximately 212° C. The backing had a total thickness of 0.0047 inches (119 micrometers). | 3M |
| Release liner | Polypropylene fluoropolymer release liner obtained under the trade designation 3M 9955 MEDICAL RELEASE LINER | 3M |

Test Methods

Caliper Measurements of Dry Gel Adhesive Test Method

Caliper measurements of the resulting gel adhesive samples were measured using a DIGIMATIC Indicator (ID-110E Series Model 543-221-1, Mitutoyo American Corporation, Aurora, Ill., USA) equipped with a 8 millimeter (mm) flat tip. The indicator was first zeroed by placing only the backing film in the indicator. Then, a caliper measurement was made in three different locations on each gel adhesive. Values were averaged to obtain those reported in the tables.

Dry 180 Degree Peel Adhesion on Stainless Steel Test Method

An IMASS-2100 peel testing instrument from Instrumentors Inc. (Strongsville, Ohio, USA) equipped with a 25 pound (11.3 kilogram (kg)) load cell was used for all peel measurements. A 1 inch (2.54 centimeters (cm)) wide sample was applied to a horizontally positioned clean stainless steel (SS) test panel. A 2.2 kg rubber roller was used to press a 4 inch (10.16 cm) length of specimen into firm contact with the SS surface. The roller was run back and forth twice over each sample. The free end of the specimen was doubled back, nearly touching itself, so the angle of removal was 180°. The free end was clamped in the load cell apparatus, while the SS test panel was adhered to the moveable platen on the instrument. This platen moved the test panel away from the load cell at a constant rate of 12 inches (30.48 cm) per minute. The average peel force as the tape was peeled from the SS panel, in ounces, was recorded. The resulting peel adhesion is reported in ounces/inch. Four to six measurements were averaged to obtain values reported in the tables.

Wet 180 Degree Peel Adhesion on Stainless Steel Test Method 1 inch by 4 inch samples were soaked in deionized (DI) water for 2 minutes. Samples were then removed from the water and applied directly on a clean stainless steel plate. A 2.2 kg roller was rolled back and forth over each sample twice before peel testing. The same peel testing protocol used for dry samples was used for the wet samples at this point. The resulting peel adhesion is reported in ounces/inch. Four to six measurements were averaged to obtain values reported in the tables.

Solubility & Gel Content Test Method

The solubility of representative uncrosslinked samples (i.e. mixture prior to being subjected to radiation) was tested by placing 30-50 milligrams (mg) of the mixture in 1 g of ethyl acetate at ambient temperature (25° C.) for 24 hours.

The gel content after crosslinking of representative samples was measured using ethyl acetate. Three one-inch diameter punch samples of each silicone gel adhesive were weighed (50-100 mg weight range of silicone gel adhesive) and placed in 2 g of ethyl acetate at ambient temperature (25° C.) for 24 hours. The samples were removed from the ethyl acetate and dried at 70° C. for 20-30 minutes. The samples were then weighed and the gel content was determined by the following equation.

[(initial adhesive weight-final adhesive weight)/initial adhesive weight]×100%.

General Procedure for Acrylic Polymers Prepared without Solvent

A reaction mixture was prepared with 58.5 parts isooctyl acrylate (IOA), 26.5 parts of PEG-acrylate in isooctyl acrylate (PEG) (~57% by mass), 15 parts acrylic acid (AA), 0.10 parts isooctyl thioglycolate (IOTG), 0.0625 parts acryloxyethoxy benzophenone (AeBP) (~50% in ethyl acetate) and various thermal initiators and antioxidants. The reaction mixture (including IOA, PEG, AA, and IOTG as appropriate) was reacted in a first reaction step, after which the various additional thermal initiators, 0.0625 parts AeBP (~50% in ethyl acetate), and antioxidants were added and a second reaction step was performed. (The combinations of thermal initiators and antioxidants used and the procedure followed the general teachings outlined in the Examples of U.S. Pat. No. 7,968,661 (Ellis and Stark).) The thermal initiators and acryloxyethoxy benzophenone were provided in ethyl acetate to ensure that they were dissolved, thus a very small amount of solvent was present in this nominally solventless reaction mixture.

Other acrylic polymers were prepared without solvent in the same manner. The kinds and amounts of monomers of the other acrylic polymers is described in the following tables.

General Procedure for Acrylic Polymers Prepared with Solvent

A reaction mixture was prepared with a ratio of 70 parts IOA, 15 parts of PEG-acrylate as a 50% solution in toluene, 15 parts AA, and thermal initiator. The reaction mixture was subsequently diluted to approximately 50 wt % in solvent. The reaction mixture was deoxygenated and heated to 60-70° C. to initiate polymerization. Other acrylic polymers were prepared with solvent in the same manner. The kinds and amounts of monomers of the other acrylic polymers is described in the following tables.

Inherent Viscosity (IV) Measurement Test Method

The inherent viscosities (IV) were obtained using a Cannon-Fenske #50 viscometer (Cannon Instrument Co., State College, Pa., USA) in a water bath controlled at 25° C. to measure the flow time of 10 milliliters (mL) of a polymer solution (0.15-0.30 g per deciliter polymer in ethyl acetate or tetrahydrofuran). The test procedure followed and the apparatus used are described in detail in Textbook of Polymer Science, F. W. Billmeyer, Wiley-Interscience, Second Edition, 1971, pages 84 and 85.

Mixtures Prepared with Solvent:

Control formulations were prepared from a non-functional and/or hydroxy-functional PDMS, typically in combination with MQ silicate resin. In a representative example, acrylic polymers were diluted/dissolved in ethyl acetate such that the final concentration was 50 wt % solids. Varying amounts of acrylic solutions were added directly to the Control formulation. For example, EX-1 was prepared using 90 wt % of Control 80/20 and 10 wt % of acrylic polymer IOA/PEG/AA 70/15/15 (50 wt % solids in ethyl acetate) such that the final composition was 95 wt % of the Control 80/20 and 5 wt % of the acrylic polymer IOA/PEG/AA 70/15/15. Each formulation was placed in a polypropylene 100 max speed cup and speedmixed in a FlackTek, Inc. DAC 150.1 FVZ-K speedmixer (Landrum, S C, USA) for 2 minutes at 1800 revolutions per minute (RPM), then subsequently speedmixed for an additional 2 minutes at 1800 RPM. The mixtures were rolled at a slow speed until used for coating. Each component started out clear and the mixed formulations were opaque. Formulations are summarized in Tables 2 and 5.

Mixtures Prepared without Solvent:

A mixture of silicone and MQ resin were put into a twin-screw extruder (MC 15 Microcompounder from Xplore Instruments, Sittard, Netherlands) and acrylic polymer (100% solids) was added to the silicone/MQ mixture at the correct concentration. The extruder was run between 130 and 150° C. with a speed of 100 RPM. Formulations are summarized in Tables 2, 3, and 4.

TABLE 2

Control 80/20 and Mixtures Prepared by Combining Control 80/20 with Acrylic Polymer

| EX | ACRYLIC POLYM, wt % | ACRYLIC POLYM SYNTHESIZED IN SOLVENT? | MIXTURE PREPARED WITH SOLVENT? | ACRYLIC POLYM IV | AK1000K, wt % | 803TF, wt % | ACRYLIC POLYM, wt % solid content |
|---|---|---|---|---|---|---|---|
| CE-1 | Control 80/20 | N/A | NO | N/A | 80 | 20 | 0 |
| EX-1 | IOA/PEG/AA 70/15/15, 5 | YES | YES | 0.9 | 76 | 19 | 5 |
| EX-2 | IOA/PEG/AA 70/15/15, 10 | YES | YES | 0.9 | 72 | 18 | 10 |
| EX-3 | IOA/PEG/AA 70/15/15, 15 | YES | YES | 0.9 | 68 | 17 | 15 |
| EX-4 | IOA/PEG/AA 70/15/15, 20 | YES | YES | 0.9 | 64 | 16 | 20 |
| EX-5 | IOA/PEG/AA 70/15/15, 25 | YES | YES | 0.9 | 60 | 15 | 25 |
| EX-6 | IOA/AA 90/10, 10 | NO | YES | 0.42 | 72 | 18 | 10 |
| EX-7 | IOA/AA 90/10, 20 | NO | YES | 0.42 | 64 | 16 | 20 |
| EX-8 | IOA/AA 98/2, 10 | NO | YES | 0.52 | 72 | 18 | 10 |
| EX-9 | IOA/AA 98/2, 20 | NO | YES | 0.52 | 64 | 16 | 20 |
| EX-10 | IOA/PEG/AA, 90/5/5 10 | NO | YES | 0.50 | 72 | 18 | 10 |
| EX-11 | IOA/PEG/AA, 90/5/5 20 | NO | YES | 0.50 | 64 | 16 | 20 |
| EX-12 | IOA/PEG/AA 70/15/15, 10 | NO | YES | 0.41 | 72 | 18 | 10 |

TABLE 2-continued

Control 80/20 and Mixtures Prepared by Combining Control 80/20 with Acrylic Polymer

| EX | ACRYLIC POLYM, wt % | ACRYLIC POLYM SYNTHESIZED IN SOLVENT? | MIXTURE PREPARED WITH SOLVENT? | ACRYLIC POLYM IV | WEIGHT PERCENT SOLIDS (SOLVENT EVAPORATED) | | |
|---|---|---|---|---|---|---|---|
| | | | | | AK1000K, wt % | 803TF, wt % | ACRYLIC POLYM, wt % solid content |
| EX-13 | IOA/PEG/AA 70/15/15, 20 | NO | YES | 0.41 | 64 | 16 | 20 |
| EX-14 | IAO/AA/PEG 75/15/15, 5 | NO | NO | 0.41 | 76 | 19 | 5 |
| EX-15 | IAO/AA/PEG 75/15/15, 10 | NO | NO | 0.41 | 72 | 18 | 10 |
| EX-16 | IAO/AA/PEG 75/15/15, 15 | NO | NO | 0.41 | 68 | 17 | 15 |
| EX-17 | IAO/AA/PEG 75/15/15, 20 | NO | NO | 0.41 | 64 | 16 | 20 |
| EX-18 | IOA/HPA 90/10, 10 | NO | NO | NT | 72 | 18 | 10 |
| EX-19 | IOA/HPA 90/10, 20 | NO | NO | NT | 64 | 16 | 20 |

TABLE 3

Control 60/40 and Mixtures Prepared by Combining Control 60/40 with Acrylic Polymer

| EX | ACRYLIC POLYM, wt % | ACRYLIC POLYM SYNTHESIZED IN SOLVENT? | MIXTURE PREPARED WITH SOLVENT? | ACRYLIC POLYM IV | WEIGHT PERCENT SOLIDS | | |
|---|---|---|---|---|---|---|---|
| | | | | | AK1000K, wt % | 803TF, wt % | ACRYLIC POLYM, wt % solid content |
| CE-2 | Control 60/40 | N/A | NO | N/A | 60 | 40 | N/A |
| EX-20 | IOA/PEG/AA 70/15/15, 15 | NO | NO | 0.41 | 51 | 34 | 15 |
| EX-21 | IOA/PEG/AA 70/15/15, 20 | NO | NO | 0.41 | 48 | 32 | 20 |
| EX-22 | IOA/PEG/AA 70/15/15, 25 | NO | NO | 0.41 | 45 | 30 | 25 |

TABLE 4

Mixtures Without Silicate Tackifying Resin

| EX | ACRYLIC POLYM, wt % | ACRYLIC POLYM SYNTHESIZED IN SOLVENT? | MIXTURE PREPARED WITH SOLVENT? | ACRYLIC POLYM IV | WEIGHT PERCENT SOLIDS | | |
|---|---|---|---|---|---|---|---|
| | | | | | AK1000K, wt % | 803TF, wt % | ACRYLIC POLYM, wt % solid content |
| EX-23 | IAO/AA/PEG 75/15/15, 10 | NO | NO | 0.41 | 90 | 0 | 10 |
| EX-24 | IAO/AA/PEG 75/15/15, 15 | NO | NO | 0.41 | 85 | 0 | 15 |

TABLE 5

Control 69/31 and Mixtures Prepared by Combining Control 69/31 with Acrylic Polymer

| EX | ACRYLIC POLYM, wt % | ACRYLIC POLYM SYNTHESIZED IN SOLVENT? | MIXTURE PREPARED WITH SOLVENT? | ACRYLIC POLYM IV | WEIGHT PERCENT SOLIDS (SOLVENT EVAPORATED) | | |
|---|---|---|---|---|---|---|---|
| | | | | | OHX-4070, wt % | 803TF, wt % | ACRYLIC POLYM, wt % solid content |
| CE-3 | Control 69/31 | N/A | NO | N/A | 69 | 31 | 0 |
| EX-25 | IOA/PEG/AA 70/15/15, 5 | YES | YES | 0.9 | 65.6 | 29.5 | 5.0 |

TABLE 5-continued

Control 69/31 and Mixtures Prepared by Combining Control 69/31 with Acrylic Polymer

| EX | ACRYLIC POLYM, wt % | ACRYLIC POLYM SYNTHESIZED IN SOLVENT? | MIXTURE PREPARED WITH SOLVENT? | ACRYLIC POLYM IV | WEIGHT PERCENT SOLIDS (SOLVENT EVAPORATED) | | ACRYLIC POLYM, wt % solid content |
|---|---|---|---|---|---|---|---|
| | | | | | OHX-4070, wt % | 803TF, wt % | |
| EX-26 | IOA/PEG/AA 70/15/15, 10 | YES | YES | 0.9 | 62.1 | 27.9 | 10.0 |
| EX-27 | IOA/PEG/AA 70/15/15, 15 | YES | YES | 0.9 | 58.7 | 26.4 | 15.0 |
| EX-28 | IOA/PEG/AA 70/15/15, 20 | YES | YES | 0.9 | 55.2 | 24.8 | 20.0 |

Coating and Processing of Resin Formulations

Samples were coated on the thermoplastic polyester elastomer layer of the backing at varying thicknesses with a desired dry thickness of 5 mil using a notch bar coater. Samples were processed with an e-beam instrument (Model CB-300, Energy Sciences, Inc., Wilmington, Mass., USA), exposed to radiation energy as indicated in the tables below at 280 kilovolts (kV). Samples were then covered with release liner. Caliper measurements were collected according to the Caliper Measurements of Dry Gel Adhesive Test Method described above and are listed in Tables 6, 7, and 8.

TABLE 6

Caliper measurements of processed gel adhesives

| Example | Thickness, mil (mm) |
|---|---|
| CE-1 | 5.2 (0.13) |
| EX-1 | 5.3 (0.13) |
| EX-2 | 4.7 (0.12) |
| EX-3 | 4.2 (0.11) |
| EX-4 | 5.4 (0.14) |
| EX-5 | 6.0 (0.15) |
| EX-6 | 3.9 (0.099) |
| EX-7 | 3.8 (0.097) |
| EX-8 | 3.5 (0.089) |
| EX-9 | 3.7 (0.094) |
| EX-10 | 3.8 (0.097) |
| EX-11 | 4.2 (0.11) |
| EX-12 | 4.3 (0.11) |
| EX-13 | 4.3 (0.11) |
| EX-14 | 4.5 (0.11) |
| EX-15 | 4.4 (0.11) |
| EX-16 | 5.3 (0.13) |
| EX-17 | 4.3 (0.11) |
| EX-18 | 5.4 (0.14) |
| EX-19 | 5.5 (0.14) |
| EX-23 | 4.2 (0.11) |
| EX-24 | 2.9 (0.074) |

TABLE 7

Caliper measurements of processed gel adhesives

| Example | Thickness, mil (mm) |
|---|---|
| CE-2 | NM |
| EX-20 | 3.3 (0.084) |
| EX-21 | 3.2 (0.081) |
| EX-22 | 3.2 (0.081) |

TABLE 8

Caliper measurements of processed gel adhesives

| Example | Thickness, mil (mm) |
|---|---|
| CE-3 | 3.7 (0.094) |
| EX-25 | 7.3 (0.19) |
| EX-26 | 6.1 (0.15) |
| EX-27 | 7.4 (0.19) |
| EX-28 | 7.6 (0.19) |

180 Degree Peel Adhesion Analysis 180 degree peels were performed on the samples both dry and wet according to the Dry Peel Adhesion on Stainless Steel Test Method and the Wet Peel Adhesion on Stainless Steel Test Method described previously. The results are summarized in Tables 8 to 11.

Acrylic polymers in Examples EX-1 to EX 5 and EX-25 to EX-28 were prepared by solvent polymerization at 50% solids. The equivalent acrylic polymers were made via solventless polymerization and dissolved in ethyl acetate such that final solution was at 50% solids (EX-6 to EX-13). These acrylic solutions were then combined with silicone gum (AK1000K or OHX-4070) and 803TF. Samples were also made via a completely solventless process (EX 13-EX 24) as described previously. Samples were then coated and subjected to electron beam at doses noted in Tables 9-12.

TABLE 9

Electron Beam Dose and 180 Peel Adhesion (ounces/inch) for Compositions of Table 2

| EX | ACRYLIC POLYMER, wt % | 2.7 Mrad Dry Average ± StdDev | 2.7 Mrad Wet Average ± StdDev | 3 Mrad Dry Average ± StdDev | 3 Mrad Wet Average ± StdDev |
|---|---|---|---|---|---|
| CE-1 | Control 80/20 | 12.5 ± 0.4 | 12.8 ± 0.5 | 12.1 ± 0.4 | 11.5 ± 0.5 |
| EX-1 | IOA/PEG/AA 70/15/15, 5 | 15.4 ± 0.7 | 15.8 ± 0.7 | 10.2 ± 1.3 | 12.1 ± 0.2 |
| EX-2 | IOA/PEG/AA 70/15/15, 10 | 18.5 ± 0.9 | 16.2 ± 0.6 | 18.7 ± 0.4 | 14.7 ± 0.5 |
| EX-3 | IOA/PEG/AA 70/15/15, 15 | 13.8 ± 1.4 | 14.8 ± 0.7 | 14.5 ± 0.8 | 13.7 ± 0.6 |

TABLE 9-continued

Electron Beam Dose and 180 Peel Adhesion (ounces/inch) for Compositions of Table 2

| EX | ACRYLIC POLYMER, wt % | 2.7 Mrad Dry Average ± StdDev | 2.7 Mrad Wet Average ± StdDev | 3 Mrad Dry Average ± StdDev | 3 Mrad Wet Average ± StdDev |
|---|---|---|---|---|---|
| EX-4 | IOA/PEG/AA 70/15/15, 20 | 17.9 ± 0.7 | 17.0 ± 0.6 | 16.7 ± 0.5 | 15.4 ± 0.8 |
| EX-5 | IOA/PEG/AA 70/15/15, 25 | 19.4 ± 0.7 | 17.3 ± 0.2 | 14.1 ± 0.8 | 15.0 ± 0.7 |
| EX-6 | IOA/AA 90/10, 10 | 12.0 ± 1.1 | 11.5 ± 0.8 | 11.0 ± 1.2 | NM |
| EX-7 | IOA/AA 90/10, 20 | 13.0 ± 0.4 | 14.6 ± 0.5 | 9.6 ± 0.6 | NM |
| EX-8 | IOA/AA 98/2, 10 | 13.4 ± 0.6 | 14.4 ± 0.8 | 12.8 ± 0.4 | NM |
| EX-9 | IOA/AA 98/2, 20 | 11.0 ± 0.7 | 11.5 ± 0.4 | 15.1 ± 0.8 | NM |
| EX-10 | IOA/PEG/AA 90/5/5, 10 | 11.9 ± 0.6 | 12.6 ± 0.6 | 13.2 ± 0.5 | NM |
| EX-11 | IOA/PEG/AA 90/5/5, 20 | 15.0 ± 1.1 | 16.3 ± 1.0 | 14.8 ± 0.8 | NM |
| EX-12 | IOA/PEG/AA 70/15/15, 10 | 16.7 ± 1.2 | 12.1 ± 1.4 | 15.1 ± 0.3 | NM |
| EX-13 | IOA/PEG/AA 70/15/15, 20 | 17.9 ± 0.4 | 12.4 ± 0.4 | 17.9 ± 0.4 | NM |
| EX-14 | IAO/AA/PEG 75/15/15, 5 | 14.2 ± 1.3 | 18.1 ± 0.4 | 16.4 ± 0.4 | 16.8 ± 0.9 |
| EX-15 | IAO/AA/PEG 75/15/15, 10 | 24.5 ± 0.3 | 20.3 ± 1.2 | 22.5 ± 0.5 | 23.1 ± 1.3 |
| EX-16 | IAO/AA/PEG 75/15/15, 15 | 25.9 ± 0.6 | 24.6 ± 0.6 | 26.6 ± 0.5 | 21.4 ± 1.4 |
| EX-17 | IAO/AA/PEG 75/15/15, 20 | 19.4 ± 1.3 | 20.1 ± 0.5 | NM | NM |
| EX-18 | IOA/HPA 90/10, 10 | 12.39 ± 1.11 | NM | 9.60 ± 0.55 | NM |
| EX-19 | IOA/HPA 90/10, 20 | 11.64 ± 0.21 | NM | 8.63 ± 0.45 | NM |

TABLE 10

Electron Beam Dose and 180 Peel Adhesion (ounces/inch) for Compositions of Table 3

| EX | ACRYLIC POLYMER, wt % | 2.5 Mrad Dry Average ± StdDev | 2.8 Mrad Dry Average ± StdDev | 3.1 Mrad Dry Average ± StdDev | 3.4 Mrad Dry Average ± StdDev |
|---|---|---|---|---|---|
| CE-2 | Control 60/40 | 16.0 ± 0.5 | 14.2 ± 0.3 | 11.9 ± 1.1 | 9.1 ± 0.5 |
| EX-20 | IOA/PEG/AA 70/15/15, 15 | 18.3 ± 0.8 | 12.0 ± 0.6 | 11.6 ± 0.9 | 14.4 ± 0.6 |
| EX-21 | IOA/PEG/AA 70/15/15, 20 | NM | 19.8 ± 0.6 | 16.5 ± 1.2 | 15.1 ± 0.5 |
| EX-22 | IOA/PEG/AA 70/15/15, 25 | NM | 16.5 ± 0.9 | 15.3 ± 0.8 | 14.6 ± 0.5 |

TABLE 11

Electron Beam Dose and 180 Peel Adhesion (ounces/inch) for Compositions of Table 4

| EX | ACRYLIC POLYMER, wt % | 3 Mrad Dry Average ± StdDev | 3 Mrad Wet Average ± StdDev | 3.3 Mrad Dry Average ± StdDev | 3.3 Mrad Wet Average ± StdDev |
|---|---|---|---|---|---|
| EX-23 | IAO/AA/PEG 75/15/15, 10 | 4.11 ± 1.03 | NM | 2.12 ± 0.12 | NM |
| EX-24 | IAO/AA/PEG 75/15/15, 15 | 3.56 ± 0.89 | NM | 1.87 ± 0.44 | NM |

TABLE 12

Electron Beam Dose and 180 Peel Adhesion (ounces/inch) for Compositions of Table 5

| EX | ACRYLIC POLYMER, wt % | 6.7 Mrad Dry Average ± StdDev | 6.7 Mrad Wet Average ± StdDev | 7 Mrad Dry Average ± StdDev | 7 Mrad Wet Average ± StdDev | 7.3 Mrad Dry Average ± StdDev | 7.3 Mrad Wet Average ± StdDev |
|---|---|---|---|---|---|---|---|
| CE-3 | Control 69/31 | 8.1 ± 0.4 | 7.7 ± 0.3 | 6.3 ± 0.1 | 6.8 ± 0.4 | 6.6 ± 0.4 | NM |
| EX-25 | IOA/PEG/AA 70/15/15, 5 | 12.3 ± 0.6 | 10.3 ± 1.0 | 6.6 ± 1.1 | 9.4 ± 0.3 | 8.6 ± 0.5 | NM |
| EX-26 | IOA/PEG/AA 70/15/15, 10 | 13.4 ± 0.1 | 9.7 ± 0.4 | 9.1 ± 0.6 | 10.2 ± 0.5 | 9.6 ± 0.3 | NM |
| EX-27 | IOA/PEG/AA 70/15/15, 15 | 10.7 ± 0.4 | 9.7 ± 0.8 | 10.0 ± 0.6 | 9.2 ± 1.0 | 11.3 ± 0.5 | NM |
| EX-28 | IOA/PEG/AA 70/15/15, 20 | 13.3 ± 0.2 | 11.9 ± 0.4 | 10.9 ± 1.0 | 10.2 ± 0.2 | 11.1 ± 0.4 | NM |

Solubility in Ethyl Acetate

The solubility of the uncrosslinked mixtures of CE-1, EX-3, CE-3, and EX-27 was tested using the test method previously described. These uncrosslinked mixtures were fully soluble in ethyl acetate.

Gel Content

The gel content of representative samples was measured after (e.g. e-beam) cross-linking using the test method previously described. The results are in Table 14 below.

TABLE 13

| EX | GEL CONTENT, % Average ± StdDev |
|---|---|
| CE-1 | 49.1 ± 1.1 |
| EX-3 | 46.8 ± 0.4 |
| CE-3 | 44.2 ± 0.6 |
| EX-27 | 64.3 ± 3 |

All cited references, patents, and patent applications in the above application for letters patent are herein incorporated by reference in their entirety in a consistent manner. In the event of inconsistencies or contradictions between portions of the incorporated references and this application, the information in the preceding description shall control. The preceding description, given in order to enable one of ordinary skill in the art to practice the claimed disclosure, is not to be construed as limiting the scope of the disclosure, which is defined by the claims and all equivalents thereto.

What is claimed is:

1. A method of making a silicone gel adhesive comprising:
    providing an acrylic polymer, the acrylic polymer comprising at least 50 wt.-% of polymerized units of $C_1$-$C_{32}$ (meth)acrylate ester monomer;
    providing at least one non-functional polydiorganosiloxane, hydroxy-functional polydiorganosiloxane, or a mixture thereof;
    combining the acrylic polymer and polydiorganosiloxane into a mixture;
    coating the mixture onto a substrate, and subjecting the mixture to radiation thereby crosslinking the mixture, and forming a silicone gel adhesive with a gel content of at least 20 wt %.

2. The method of claim 1 wherein the provided polydiorganosiloxane consists of one or more non-functional polydimethylsiloxanes that lack functional groups such that the non-functional polydimethylsiloxanes do not covalently bond with the acrylic polymer prior to subjecting the mixture to radiation.

3. The method of claim 1 wherein the provided polydiorganosiloxane(s) consist of one or more hydroxy-functional polydimethylsiloxanes.

4. The method of claim 3 wherein the hydroxy-functional polydimethylsiloxane(s) form covalent bond via condensation reactions and/or by reaction with the acrylic polymer.

5. The method of claim 1 wherein the acrylic polymer is present in an amount ranging from 5 to 30 wt.-% of the adhesive.

6. The method of claim 1 wherein the acrylic polymer comprises at least 50 wt.-% of polymerized units of C1-C32 (meth)acrylate ester monomer(s) wherein a homopolymer of said monomer(s) has a Tg no greater than 0° C.

7. The method of claim 6 wherein the acrylic polymer further comprises up to 35 wt.-% of polymerized units of ethylenically unsaturated acidic monomer(s).

8. The method of claim 6 wherein the acrylic polymer further comprises up to 35 wt.-% of polymerized units of non-acidic polar monomer(s).

9. The method of claim 1 wherein the silicone gel adhesive further comprises a silicate resin tackifier.

10. The method of claim 1 wherein the step of combining the acrylic polymer and non-functional polydiorganosiloxane(s) and/or hydroxy-functional polydiorganosiloxane(s) comprises mixing, blending, milling, extrusion, or combinations thereof.

11. The method of claim 10 wherein the step of combining further comprises adding an organic solvent or lacks an organic solvent.

12. The method of claim 1 wherein 30 milligrams of the mixture is soluble in 1 gram of ethyl acetate before subjecting the mixture to radiation.

* * * * *